United States Patent [19]

Yoshimoto et al.

[11] Patent Number: 4,551,478

[45] Date of Patent: * Nov. 5, 1985

[54] 3-NITROBENZENE SULFONANILIDE DERIVATIVES AND FUNGICIDAL COMPOSITIONS FOR THE CONTROL OF PLANT DISEASES CONTAINING SAME

[75] Inventors: Tekeo Yoshimoto, Yokohama; Mitsumasa Umemoto, Ohmuta; Keiichi Igarashi, Musashino; Hideo Yamazaki, Yokohama; Yoshio Takasawa, Ayase; Hirohisa Yanagita, Chigasaki, all of Japan

[73] Assignee: Mitsui Toatsu Chemicals, Inc., Tokyo, Japan

[ * ] Notice: The portion of the term of this patent subsequent to Feb. 5, 2002 has been disclaimed.

[21] Appl. No.: 454,634

[22] Filed: Dec. 30, 1982

[30] Foreign Application Priority Data

Jun. 16, 1982 [JP] Japan ............................ 57-102080

[51] Int. Cl.[4] .................... C07C 143/79; A01N 41/06
[52] U.S. Cl. ...................................... 514/603; 564/87
[58] Field of Search .................. 564/87; 424/321; 514/603

[56] References Cited

U.S. PATENT DOCUMENTS 3,034,955  5/1962  Frick et al. .................. 564/87 X
3,804,586  4/1974  Kalopissis et al. ............ 564/87 X
4,021,229  5/1977  Arneklev et al. .............. 71/100
4,113,463  9/1978  Ashio et al. .................. 564/87 X

FOREIGN PATENT DOCUMENTS 1163838  2/1964  Fed. Rep. of Germany ........ 564/87
0015119  5/1972  Japan .
0031655  2/1982  Japan ........................ 424/321

OTHER PUBLICATIONS

Dauphin et al., CA 56:7194d (1962).
Dauphin et al., CA 68:29383s and 29384t (1968).
Mikhailova et al., CA 85:62996t (1976).
Litvinenko et al., CA 80:36578k (1974).
Bell, J. Chem. Soc. 1930, pp. 1071–1077 (1930).
Krasha et al., CA 95:82381y (1981).
Srivastava, CA 68:12627b (1968).

Primary Examiner—Thomas A. Waltz
Attorney, Agent, or Firm—Fisher, Christen & Sabol

[57] ABSTRACT

Disclosed are novel 3-nitrobenzene sulfonanilide derivatives and, among others, that of the formula

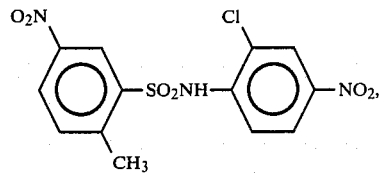

as well as fungicidal compositions containing such compounds as the active ingredient. The compounds of the invention are markedly effective in controlling plant diseases and, in particular, clubroot disease of Brassica spp., have no toxicity to men, beasts, and fishes, exert no phytotoxicity on crops, have neither irritant nor unpleasant odor, and manifest their excellent fungicidal effect at low concentrations. Accordingly, they are ideally useful in fungicidal compositions.

8 Claims, No Drawings

3-NITROBENZENE SULFONANILIDE DERIVATIVES AND FUNGICIDAL COMPOSITIONS FOR THE CONTROL OF PLANT DISEASES CONTAINING SAME

TECHNICAL FIELD

This invention relates to novel 3-nitrobenzene sulfonanilide derivatives and fungicidal compositions for the control of plant diseases containing such compounds as the active ingredient.

BACKGROUND ART

It is an important problem in agriculture to diminish or eliminate injury by continuous cropping. Especially in countries and districts having a limited area of cultivated land, crops must be repeatedly planted through the year and, therefore, continuous cropping is unavoidable.

Under these conditions, biological factors associated with the soil interfere with the growth of various crops such as vegetables, legumes, potatoes, strawberry, tobacco, devil's-tongue, chrysanthemum, carnation, stock, mulberry, apple tree, upland rice, and the like, so that farmers suffer heavy losses. Moreover, the situation goes on getting worse from year to year.

Conventionally, the control of plant diseases and, in particular, soil-borne diseases is very difficult and there is a continuing demand for the development of excellent fungicides. By way of example, the damage due to clubroot disease of Brassica spp. shows a tendency to increase from year to year. That is, important vegetables (such as cabbages, Chinese cabbages, turnips, and the like) indispensable to the dietary life of men are being considerably damaged by this Clubroot disease.

At present, various attempts are being made to control soil-borne diseases by means of fungicides. However, commercially available fungicides fail to produce desirable results and cannot be regarded as preferable from a practical point of view. More specifically, in the existing circumstances, none of the commercially available soil fungicides are satisfactory because they have the disadvantages of failing to produce their fungicidal effect unless used at high concentrations, tending to remain in the crop plants or the soil, having very high toxicity to men and beasts, tending to exert phytotoxicity on the crop, and/or having an irritant or an unpleasant odor.

For example, mercury compounds have very high toxicity and volatile substances such as methyl bromide and chloropicrin tend to give off a toxic and irritant gas, so that they may give rise to the problem of environmental pollution. Pentachloronitrobenzene (PCNB) fails to effectively control clubroot disease of Brassica spp., unless applied to the crop in large amounts. Moreover, this compound can hardly be decomposed owing to its stable chemical structure, thus involving a possibility of soil pollution. Furthermore, PCNB tends to be accompanied by hexachlorobenzene, as an impurity, which is difficult to separate during the manufacture of PCNB. It is well known that this compound is undesirable because it remains in the soil for a long period of time and also has high toxicity. Besides, methyl isothiocyanate requires repeated degassing operations in order to avoid its phytotoxicity. Nevertheless, the possibility of phytotoxicity cannot completely be eliminated.

Benzene sulfonanilide and its derivatives are known for a long time, but only a little is known about analogous compounds having their aromatic ring substituted by a nitro group. Japanese Patent Publication No. 41638/'71 discloses 2-nitrobenzene sulfone-2,4-dichloroanilide which is effective in controlling citrus canker. Japanese Patent Publication No. 15119/'72 discloses three nitro-substituted benzene sulfonanilides (i.e., 3-nitrobenzene sulfonanilide, 3-nitrobenzene sulfone-4-chloroanilide, and 3-nitrobenzene sulfone-3,4-dichloroanilide), which are described as being effective in controlling brown leaf spot and pellicularia disease of rice. Japanese Patent Laid-Open No. 31655/'82 discloses 2-nitrobenzene sulfone-2,6-diethylanilide, which is described as being effective in controlling rice blast.

As described above, a number of nitro-substituted benzene sulfonanilides are known in the prior art. However, nothing is known about the nitro-substituted benzene sulfonanilides having both aromatic rings substituted by nitro groups or having the benzenesulfonyl group substituted by both a nitro group and an alkyl radical as well as the 3-nitrobenzene sulfonanilide derivatives having a halogen substituent at the 2-position of the anilino group or having a halogen substituent only at the 3-position of the anilino group. Moreover, neither experiment on the ability of benzene sulfonanilide and its derivatives to control soil-borne diseases, nor literature disclosing their effectiveness in controlling soil-borne diseases can be found.

DISCLOSURE OF THE INVENTION

It is an object of the present invention to provide novel 3-nitrobenzene sulfoanilide derivatives.

It is another object of the present invention to provide novel fungicidal compositions which are markedly effective in controlling plant diseases and, in particular, clubroot disease of Brassica spp.

The above objects of the present invention are accomplished by providing, as novel compounds, 3-nitrobenzene sulfonanilide derivatives having the general formula

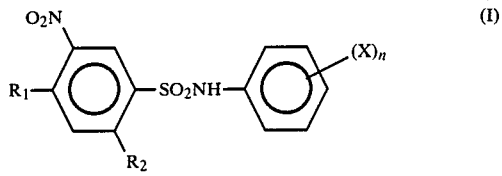 (I)

where $R_1$ and $R_2$ each represent a hydrogen atom or a methyl radical, X represents a halogen atom, a methyl radical, or a nitro group, n is a whole number of 1 to 3, and when n is equal to 2 or 3, the atoms or radicals represented by X may be identical to or different from each other, but the two compounds in which $R_1$ and $R_2$ are both hydrogen atoms and $(X)_n$ is 4-chloro or 3,4-dichloro and the compound in which $R_1$ is a methyl radical, $R_2$ is a hydrogen atom and $(X)_n$ is 2-chloro-4-nitro are excluded, as well as by providing fungicidal compositions for the control of plant diseases which contain such compounds as the active ingredient.

The compounds of the present invention have neither toxicity to men and beasts nor toxicity to fishes and shellfishes, exert no phytotoxicity on crops, have neither irritant nor unpleasant odor, and can control plant diseases at so low concentrations that the amount of fungicide used and hence the possibility of soil pollution can be diminished. Thus, these compounds can ideally be used as fungicides for the control of plant diseases.

BEST MODE FOR CARRYING OUT THE INVENTION

The melting points, as well as the results of elemental analysis, of compounds typical of the 3-nitrobenzene sulfonanilide derivatives of the present invention are shown in Table 1.

The 3-nitrobenzene sulfonanilide derivatives of the present invention can be prepared by reacting a corresponding 3-nitrobenzene sulfonyl chloride derivative with a corresponding aniline derivative in the presence of pyridine. The reaction may suitably be carried out in inert solvents such as toluene, xylene, nitrobenzene, and the like. However, where pyridine is used in large amounts, it can also be utilized as the solvent. The reaction temperature can range from 70° to 200° C., the preferred range being from 100° to 140° C. The reaction time can range from 5 to 30 hours, the preferred range being from 5 to 20 hours.

The method for preparing the compounds of the present invention is more specifically explained with reference to the following examples.

EXAMPLE 1

[Synthesis of 3-nitrobenzene sulfone-2-chloro-4-nitroanilide (Compound No. 26)]

TABLE 1

| Compound No. | Substituents in general formula (I) | | | Melting point (°C.) | Elemental analysis (%) [found value/(calculated value)] | | | | |
|---|---|---|---|---|---|---|---|---|---|
| | $R_1$ | $R_2$ | $(X)_n$ | | C | H | N | S | Halogen |
| 1 | $CH_3$ | H | 4-I | 136–138 | 37.29 (37.32) | 2.67 (2.63) | 6.37 (6.70) | 7.71 (7.66) | 30.41[I] (30.38) |
| 2 | $CH_3$ | H | 2,3-$Cl_2$ | 155.5–157 | 43.23 (43.21) | 2.80 (2.77) | 7.79 (7.76) | 8.83 (8.86) | 19.64[Cl] (19.67) |
| 3 | $CH_3$ | H | 2,4-$Cl_2$ | 144.5–146 | 43.18 (43.21) | 2.80 (2.77) | 7.75 (7.76) | 8.82 (8.86) | 19.71[Cl] (19.67) |
| 4 | $CH_3$ | H | 2,5-$Cl_2$ | 126–128 | 43.23 (43.21) | 2.74 (2.77) | 7.72 (7.76) | 8.83 (8.86) | 19.70[Cl] (19.67) |
| 5 | $CH_3$ | H | 3,5-$Cl_2$ | 137–139 | 43.19 (43.21) | 2.81 (2.77) | 7.80 (7.76) | 8.81 (8.86) | 19.71[Cl] (19.67) |
| 6 | $CH_3$ | H | 2-Br 4,5-$Cl_2$ | 169.5–171.5 | 35.51 (35.45) | 2.12 (2.05) | 6.34 (6.36) | 7.31 (7.27) | 17.99[Br] (18.18) 16.08[Cl] (16.14) |
| 7 | $CH_3$ | H | 4-$NO_2$ | 191–193 | 46.31 (46.29) | 3.32 (3.26) | 12.50 (12.46) | 9.42 (9.50) | |
| 8 | $CH_3$ | H | 2-Cl 5-$NO_2$ | 165–167 | 41.72 (41.99) | 2.64 (2.69) | 11.25 (11.31) | 8.56 (8.61) | 9.60[Cl] (9.56) |
| 9 | $CH_3$ | H | 2-$CH_3$ 5-$NO_2$ | 148–150 | 47.89 (47.86) | 3.68 (3.70) | 11.94 (11.97) | 9.09 (9.12) | |
| 10 | $CH_3$ | H | 2-$CH_3$ 6-$NO_2$ | 146–148 | 47.90 (47.86) | 3.72 (3.70) | 11.94 (11.97) | 9.16 (9.12) | |
| 11 | $CH_3$ | H | 2-$NO_2$ 4-$CH_3$ | 146.5–148.5 | 47.80 (47.86) | 3.65 (3.70) | 11.88 (11.97) | 9.23 (9.12) | |
| 12 | H | $CH_3$ | 2-Cl | 189–191.5 | 47.81 (47.78) | 3.40 (3.37) | 8.55 (8.58) | 9.77 (9.80) | 10.84[Cl] (10.87) |
| 13 | H | $CH_3$ | 4-Cl | 139.5–142 | 47.80 (47.78) | 3.40 (3.37) | 8.54 (8.58) | 9.85 (9.80) | 10.91[Cl] (10.87) |
| 14 | H | $CH_3$ | 4-F | 127–128.5 | 50.27 (50.32) | 3.60 (3.55) | 9.08 (9.03) | 10.29 (10.32) | 6.04[F] (6.13) |
| 15 | H | $CH_3$ | 4-I | 171–172.5 | 37.28 (37.32) | 2.54 (2.63) | 6.80 (6.70) | 7.52 (7.66) | 30.29[I] (30.38) |
| 16 | H | $CH_3$ | 2,4-$Cl_2$ | 167–168.5 | 43.18 (43.21) | 2.74 (2.77) | 7.80 (7.76) | 8.76 (8.86) | 19.84[Cl] (19.67) |
| 17 | H | $CH_3$ | 2,5-$Cl_2$ | 127.5–128.5 | 43.19 (43.21) | 2.79 (2.77) | 7.72 (7.76) | 8.80 (8.86) | 19.70[Cl] (19.67) |
| 18 | H | $CH_3$ | 3,5-$Cl_2$ | 184–186 | 43.30 (43.21) | 2.81 (2.77) | 7.74 (7.76) | 8.91 (8.86) | 19.64[Cl] (19.67) |
| 19 | H | $CH_3$ | 2-Br 4,5-$Cl_2$ | 177–179 | 35.49 (35.45) | 2.09 (2.05) | 6.40 (6.36) | 7.30 (7.27) | 18.09[Br] (18.18) 16.19[Cl] (16.14) |
| 20 | H | $CH_3$ | 2-Cl 4-$NO_2$ | 227–229 | 42.18 (41.99) | 2.51 (2.69) | 11.23 (11.31) | 8.57 (8.61) | 9.49[Cl] (9.56) |
| 21 | H | H | 3-Cl | 131–133 | 45.92 (46.08) | 2.74 (2.88) | 8.89 (8.96) | 10.11 (10.24) | 11.40[Cl] (11.36) |
| 22 | H | H | 2-I | 110–112 | 35.70 (35.64) | 2.19 (2.23) | 6.89 (6.93) | 7.98 (7.92) | 31.22[I] (31.44) |
| 23 | H | H | 2,4-$Cl_2$ | 143.5–144.5 | 41.62 (41.50) | 2.34 (2.31) | 8.10 (8.07) | 9.18 (9.22) | 20.09[Cl] (20.46) |
| 24 | H | H | 2,5-$Cl_2$ | 156–158 | 41.44 (41.50) | 2.29 (2.31) | 8.10 (8.07) | 9.30 (9.22) | 20.70[Cl] (20.46) |
| 25 | H | H | 2,4,6-$Cl_3$ | 210–211 | 37.64 (37.75) | 1.79 (1.83) | 7.30 (7.34) | 8.42 (8.39) | 27.88[Cl] (27.29) |
| 26 | H | H | 2-Cl 4-$NO_2$ | 179–180 | 40.31 (40.28) | 2.23 (2.24) | 11.84 (11.75) | 8.79 (8.95) | 9.89[Cl] (9.93) |
| 27 | H | H | 2-Cl 5-$NO_2$ | 213–214 | 40.33 (40.28) | 2.25 (2.24) | 11.79 (11.75) | 8.90 (8.95) | 9.92[Cl] (9.93) |

A solution was prepared by dissolving 3.4 g (0.02 mole) of 2-chloro-4-nitroaniline in 30 ml of pyridine.

While this solution was being stirred at 80°–90° C., 4.5 g (0.02 mole) of 3-nitrobenzene sulfonyl chloride was added slowly thereto. Subsequently, this mixture was stirred at 100°–110° C. for 5 hours to complete the reaction. The resulting reaction mixture was cooled to room temperature, poured into 100 ml of cold water, and allowed to stand for a while. The precipitate so formed was extracted twice by shaking with 200 ml portions of ethyl acetate. This extract was washed with water, dehydrated over anhydrous sodium sulfate, and then stripped of ethyl acetate under reduced pressure. The residue was subjected to silica gel chromatography (using a 3:1 mixture of toluene and ethyl acetate as the developing solvent) to obtain 4.3 g of a desired product in a 60% yield. This product was a pale-yellow crystalline substance, and its melting point and results of elemental analysis are shown in table 1.

EXAMPLE 2

[Synthesis of 3-nitro-4-methylbenzene sulfone-2-chloro-5-nitroanilide (Compound No. 8)]

A solution was prepared by dissolving 3.4 g (0.02 mole) of 2-chloro-5-nitroanilide and 3.2 g (0.04 mole) of pyridine in 200 ml of toluene. While this solution was being stirred at room temperature, a solution of 4.8 g (0.02 mole) of 3-nitro-4-methylbenzene sulfonyl chloride in 50 ml of toluene was slowly added thereto. Subsequently, this mixture was heated to 110° C. and stirred under reflux for 20 hours to effect the condensation reaction. After the resulting reaction mixture was stripped of toluene under reduced pressure, the residue was extracted with 200 ml of ethyl acetate. The extract was thoroughly washed with dilute hydrochloric acid and water, dehydrated over anhydrous sodium sulfate, and then stripped of ethyl acetate under reduced pressure to obtain a crude product. This crude product was subjected to silica gel chromatography (using a 5:1 mixture of toluene and ethyl acetate as the developing solvent) to obtain 4.0 g of a highly pure product in a 53.8% yield. The melting point of this product and the results of elemental analysis thereof are shown in Table 1. The values obtained by NMR and IR analysis thereof are given below.

NMR: $\delta_{TMS}^{DMSO}$ D$_6$ = 2.60 (3H, S, CH$_3$)

IR: $\nu_{max}^{KBr}$ (cm$^{-1}$) = 3220 (NH)

EXAMPLE 3

[Synthesis of 5-nitro-2-methylbenzene sulfone-2-chloro-4-nitroanilide (Compound No. 20)]

A solution was prepared by dissolving 3.4 g (0.02 mole) of 2-chloro-4-nitroaniline and 8.0 g (0.1 mole) of pyridine in 200 ml of nitrobenzene. While this solution was being stirred at room temperature, a solution of 4.8 g (0.02 mole) of 5-nitro-2-methylbenzene sulfonyl chloride in 50 ml of nitrobenzene was slowly added thereto. Subsequently, this mixture was stirred at 130°–140° C. for 10 hours to complete the reaction. After the resulting reaction mixture was allowed to cool, nitrobenzene was removed therefrom by steam distillation. The crystalline residue so formed was collected by filtration and recrystallized from ethanol to obtain 5.0 g of the desired product in a 67.3% yield. The melting point of this product and the results of elemental analysis thereof are shown in Table 1. The values obtained by NMR and IR analysis thereof are given below.

NMR: $\delta_{TMS}^{DMSO}$ D$_6$ = 2.75 (3H, S, CH$_3$)

IR: $\nu_{max}^{KBr}$ (cm$^{-1}$) = 3265 (NH)

EXAMPLE 4

In the same manner as described in Example 1, Compounds No. 2, No. 5, No. 9, No. 10, No. 15, No. 17, No. 22 and No. 27 were prepared by using suitable combinations of starting materials, i.e., 3-nitrobenzene sulfonyl chloride derivatives and aniline derivatives. The melting points of these compounds and the results of elemental analysis thereof are shown in Table 1.

EXAMPLE 5

In the same manner as described in Example 2, Compounds No. 1, No. 6, No. 7, No. 13, No. 14, No. 19, No. 21, and No. 25 were prepared by using suitable combinations of starting materials, i.e., 3-nitrobenzene sulfonyl chloride derivatives and aniline derivatives. The melting points of these compounds and the results of elemental analysis thereof are shown in Table 1.

EXAMPLE 6

In the same manner as described in Example 3, Compounds No. 3, No. 4, No. 11, No. 12, No. 16, No. 18, No. 23, and No. 24 were prepared by using suitable combinations of starting materials, i.e., 3-nitrobenzene sulfonyl chloride derivatives and aniline derivatives. The melting points of these compounds and the results of elemental analysis thereof are shown in Table 1.

The fungicidal compositions of the present invention can take any desired form suitable for use as agricultural or horticultural preparations, particularly fungicidal formulations, provided that they contain at least one compound of the above general formula (I) as the active ingredient. For example, according to the intended purpose, the compounds of the present invention may be used as such or may be combined with suitable carriers to make them into various forms such as dusts, granules, fine granules, wettable powders, flowable formulations, emulsifiable concentrates, and the like. Preferably, the amount of active ingredient present in such a composition is in the range of 2 to 5% for dusts, granules, and fine granules; in the range of 40 to 60% for wettable powders and flowable formulations; and in the range of 30 to 50% for emulsifiable concentrates.

Specific examples of useful solid carriers include clay, talc, kaolin, bentonite, diatomaceous earth, silica, calcium carbonate, calcium sulfate, and the like. Specific examples of useful liquid carriers include water, aromatic hydrocarbons, aliphatic hydrocarbons, alcohols, esters, ketones, acid amides, fatty acids, animal and vegetable oils, various surface active agents, and the like. Moreover, suitable adjuvants such as spreaders, emulsifiers, wetting agents, dispersants, sticking agents, and the like may be added in order to ensure effectiveness. Furthermore, the compounds of the present invention may be used in admixture with various agricultural materials such as herbicides, insecticides, miticides, other fungicides, soil conditioners, fertilizers, and the like, or may be used as additives.

The fungicidal compositions of the present invention can be used by sprinkling them directly on the crop plant whose disease is to be controlled. Besides, according to the need, they can be applied to the growing environment of the crop plant, i.e., the surface of the water, the ground, or the like, and can be mixed in the soil.

The amount of fungicidal composition used can vary according to the intended purpose. In the case of emulsifiable concentrates, wettable powders, and the like, it is usually desirable to spray them in the form of a dispersion which contains the active ingredient (i.e., the compound of the present invention) at a concentration of 10 to 1,000 ppm. However, where a small volume of highly concentrated dispersion is used or a dispersion is sprayed by means of aircraft, the concentration of the dispersion may be increased as desired. In the case of dusts, granules, and the like, the amount of fungicidal composition used may be changed according to the size of the crop plant, the density of the pathogenic organism, its sensitivity to the fungicide, and the like. However, they can usually be used in substantially the same amount as conventional fungicides.

Where it is desired to control clubroot disease of Brassica spp., the compounds of the present invention are preferably used as such or in any of the above-described forms and applied, prior to the planting of the crop, in such an amount as to provide 5 to 20 kg of the active ingredient per hectare.

Several examples of fungicidal compositions containing a compound of the present invention as the active ingredient are described hereinbelow. However, it is to be understood that the type and proportion of additives used are not limited thereto and the content of the active ingredient can vary widely. The compounds of the present invention which are used as the active ingredient in these fungicidal compositions have the same designations as defined in Table 1.

FUNGICIDAL COMPOSITION 1

[Dust]

A mixture of 10.5 g of Compound No. 23, 2.0 g of Carplex #80 (white carbon; a product of Shionogi Pharmaceutical Co.), and 87.5 g of clay was pulverized to form a dust.

FUNGICIDAL COMPOSITION 2

[Granules]

Pulverized Compound No. 3 (20.5 g) was intimately mixed with 2.0 g of Gohsenol GL-05S (PVA; a product of Nihon Synthetic Chemistry Co.), 2.0 g of Sun Extract p-252 (lignin sulfonic acid sodium salt; a product of Sanyo Kokushaku Pulp Co.), and 75.5 g of clay. This mixture was moistened with an appropriate amount of water and then granulated by means of an extruding machine. The resulting granules were air-dried at 60°–90° C., crushed, and then adjusted to a particle size of 0.3–1 mm by means of a classifier.

FUNGICIDAL COMPOSITION 3

[Wettable powder]

A mixture of 50.5 g of Compound No. 20, 5.0 g of Sorpol 5039 (a mixture of a special nonionic-anionic surface active agent and white carbon; a product of Toho Chemicals Co.), and 44.5 g of Radiolite #200 (calcined diatomaceous earth; a product of Showa Chemicals Co.) was pulverized to form a wettable powder.

FUNGICIDAL COMPOSITION 4

[Flowable formulation]

Compound No. 19 (40.0 g) was mixed with 10.0 g of lignin sulfonic acid sodium salt, 1.0 g of gum arabic, and 49.0 g of water. This mixture was pulverized with a sand grinder to form a flowable formulation.

Next, the effects of the present invention are discussed hereinbelow. The diseases of agricultural and horticultural crops which are at present difficult to control effectively include bactrial diseases, virus diseases, and various soil-borne diseases. The compounds of the present invention have very excellent performance as fungicides for the control of plant diseases, in that they are effective in controlling bacterial diseases (e.g., bacterial leaf blight of rice) and soil-borne diseases (e.g., clubroot disease of Brassica spp.). Their effectiveness is more fully illustrated by the following evaluation tests. The compounds used in these evaluation tests have the same designation as defined in Table 1.

EVALUATION TEST 1

[Test for protection against clubroot diseases of Brassica spp.]

A dust prepared according to the procedure of Fungicidal Composition 1 was added to and mixed in 1.0 kg of soil contaminated with the causal organism of clubroot disease of Brassica spp. (i.e., Plasmodiophora brassicae) so as to provide the specified amount of the active ingredient. This soil was charged into No. 5 pots and 20 seeds of Chinese cabbage (Brassica rupa L. var. Komatsuna Hara) were sown in each of the spots. These pots were placed on an outdoor stand. Six weeks after sowing, the roots of the growing plants were washed in running water and examined for the presence of affection. Then, the rate of protection was calculated according to the following equation.

Rate of protection (%) =

$$\frac{\text{Number of intact plants in each group}}{\text{Number of examined plants in each group}} \times 100$$

As control fungicides, the compounds described in Japanese Patent Publication No. 15119/'72 (i.e., 3-nitrobenzene sulfonanilide, 3-nitrobenzene sulfone-4-chloroanilide, and 3-nitrobenzene sulfone-3,4-dichloroanilide) were used. This test was carried out in triplicate and the rates of protection for the respective runs were averaged. The results thus obtained are shown in Table 2.

TABLE 2

| Compound No. | Amount of active ingredient per pot (mg) | | | Phytotoxicity |
|---|---|---|---|---|
| | 5 | 10 | 20 | |
| 1 | 48.0 | 56.3 | 100.0 | None |
| 2 | 24.2 | 43.2 | 96.0 | " |
| 3 | 56.6 | 97.6 | 100.0 | " |
| 4 | 55.5 | 85.6 | 100.0 | " |
| 5 | 36.1 | 66.2 | 100.0 | " |
| 6 | 61.1 | 73.0 | 100.0 | " |
| 7 | 22.5 | 90.0 | 100.0 | " |
| 8 | 91.0 | 100.0 | 100.0 | " |
| 9 | 70.4 | 92.8 | 100.0 | " |
| 10 | 61.2 | 100.0 | 100.0 | " |
| 11 | 48.8 | 71.6 | 100.0 | " |
| 12 | 86.0 | 96.5 | 100.0 | " |
| 13 | 50.3 | 96.6 | 100.0 | " |
| 14 | 78.6 | 93.2 | 100.0 | " |

TABLE 2-continued

| Compound No. | Amount of active ingredient per pot (mg) | | | Phytotoxicity |
|---|---|---|---|---|
| | 5 | 10 | 20 | |
| 15 | 54.8 | 95.6 | 100.0 | " |
| 16 | 81.4 | 100.0 | 100.0 | " |
| 17 | 72.2 | 100.0 | 100.0 | " |
| 18 | 52.8 | 74.5 | 100.0 | " |
| 19 | 68.5 | 86.9 | 100.0 | " |
| 20 | 98.9 | 100.0 | 100.0 | " |
| 21 | 92.4 | 100.0 | 100.0 | " |
| 22 | 85.9 | 100.0 | 100.0 | " |
| 23 | 94.4 | 100.0 | 100.0 | " |
| 24 | 75.6 | 98.0 | 100.0 | " |
| 25 | 72.7 | 100.0 | 100.0 | " |
| 26 | 91.5 | 100.0 | 100.0 | " |
| 27 | 90.2 | 100.0 | 100.0 | " |
| A* | 0.0 | 12.8 | 18.7 | " |
| B* | 0.0 | 10.8 | 15.8 | " |
| C* | 0.0 | 4.5 | 32.6 | " |
| No treatment | 0.0 | 0.0 | 0.0 | " |

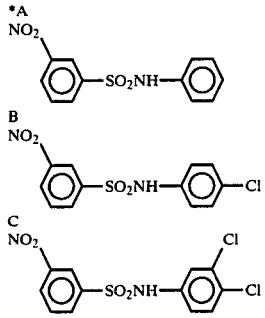

*A, B, C structures (nitro-substituted sulfonanilides)

EVALUATION TEST 2

[Test for fungicidal activity against the organism of bacterial leaf blight of rice]

In Petri dishes of 9 cm diameter, 15 ml of a 1.5% water agar medium was poured and solidified. Then, 5 ml of a test medium containing the causal organism of bacterial leaf blight of rice (i.e., *Xanthomonas oryzae*) was poured thereon and solidified to form an upper layer. A paper disc of 7 mm diameter was soaked in a 1000 ppm acetone solution of each compound to be tested for 30 minutes and then placed on the test medium. The Petri dish was incubated at 28° C. for 24 hours and the diameter of the resulting inhibited circle was measured to evaluate the fungicidal activity of the compound. The test medium had the following composition.

| Composition of Test Medium (in 1 liter of water) | |
|---|---|
| Component | Quantity |
| Sodium glutamate | 2.0 g |
| Monopotassium phosphate | 2.0 g |
| Magnesium chloride | 1.0 g |
| Ferrous sulfate | 0.1 g |
| Sucrose | 20.1 g |
| Yeast extract | 2.0 g |
| Peptone | 5.0 g |
| Agar | 15–20 g |

As control fungicides, the same compounds as used in Evaluation Test 1 (i.e., the three compounds described in Japanese Patent Publication No. 15119/'72) and streptomycin sulfate were used in the form of 1000 ppm acetone solutions. The results thus obtained are shown in Table 3.

TABLE 3

| Compound No. | Diameter of inhibited circle (cm) | Compound No. | Diameter of inhibited circle (cm) |
|---|---|---|---|
| 2 | 3.0 | 18 | 3.2 |
| 4 | 3.0 | 19 | 3.3 |
| 5 | 3.2 | 20 | 3.3 |
| 6 | 3.0 | A* | 0.0 |
| 13 | 3.0 | B* | 0.0 |
| 14 | 2.8 | C* | 0.0 |
| 15 | 2.9 | D* | 2.5 |
| 17 | 3.3 | | |

*A, B, C: See the notes to Table 2.
D: Streptomycin sulfate.

EVALUATION TEST 3

[Field test for protection against clubroot disease of Brassica spp.]

To the whole surface of a field in which this disease had habitually occurred was applied a complex fertilizer in such an amount as to provide 30 kg each of N, P₂O₅, and K₂O per 10 ares. After being plowed, the field was divided into 4 m×5 m plots each having an area of 20 m². A dust prepared according to the procedure of Fungicidal Composition 1 was uniformly spread in the specified amount and intimately mixed with the soil by means of a small cultivator. On the following day, speedlings of Chinese cabbage (var. Muso) which had been grown in paper pots for three weeks were planted with a ridge breadth of 60 cm and a distance between plants of 45 cm. Seven weeks after planting, the roots of the plants were dug out and examined for the degree of affection. The rate of affection was calculated, together with the index of affection as defined by the following equation.

$$\text{Index of affection} = \frac{0 \times n_0 + 1 \times n_1 + 2 \times n_2 + 3 \times n_3}{N}$$

where
- $n_0$: number of individuals in which no swellings are observed.
- $n_1$: number of individuals in which swellings are observed solely on lateral roots.
- $n_2$: number of individuals in which swellings are observed both on the main root and on lateral roots, but they are not marked.
- $n_3$: number of individuals in which marked swellings are observed both on the main root and on lateral roots.
- N: total number of examined individuals.

Besides, the overground portion of the plants was examined for yield. A PCNB dust (containing 20% of the active ingredient) was used as a control fungicide. This test was carried out in triplicate and the results thus obtained are shown in Table 4.

TABLE 4

| Compound No. | Amount of active ingredient used (kg/ha) | Rate of affection (%) | Index of affection | Yield* (tons/ha) | Phytotoxicity |
|---|---|---|---|---|---|
| 20 | 10 | 12.5 | 0.30 | 131.2 | None |
| | 20 | 3.0 | 0.10 | 152.0 | " |
| | 40 | 0.0 | 0.00 | 156.3 | " |
| PCNB (control) | 40 | 100.0 | 2.68 | 80.2 | None |
| | 60 | 94.5 | 2.21 | 100.2 | " |

TABLE 4-continued

| Compound No. | Amount of active ingredient used (kg/ha) | Rate of affection (%) | Index of affection | Yield* (tons/ha) | Phytotoxicity |
|---|---|---|---|---|---|
| No treatment | — | 100.0 | 3.00 | 24.0 | None |

*The weight of Chinese cabbages prepared for commercial purposes by removing 5–7 outer leaves.

We claim:

1. A 3-nitrobenzene sulfonanilide derivative having the formula:

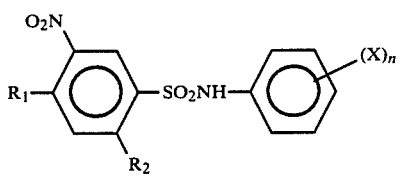

wherein $R_1$ and $R_2$ are both hydrogen, $R_1$ is hydrogen and $R_2$ is methyl or $R_1$ is methyl and $R_2$ is hydrogen, and when $R_1$ and $R_2$ are both hydrogen, $(X)_n$ is 2,4,6-trichloro, 2-chloro-4-nitro or 2-chloro-5-nitro; when $R_1$ is hydrogen and $R_2$ is methyl, $(X)_n$ is 4-iodo, 2,5-dichloro, 3,5-dichloro, 2-bromo-4,5-dichloro or 2-chloro-4-nitro; and when $R_1$ is methyl and $R_2$ is hydrogen, $(X)_n$ is 4-iodo, 2,3-dichloro, 2,5-dichloro, 3,5-dichloro, 2-bromo-4,5-dichloro, 2-chloro-5-nitro, 2-methyl-6-nitro or 2-nitro-4-methyl.

2. The 3-nitrobenzene sulfonanilide derivative of claim 1 wherein, in the general formula (I), $(X)_n$ is 2-chloro-4-nitro.

3. A fungicidal composition for controlling soil-borne plant diseases containing, as the active ingredient, in the range of 2 to 5 weight percent for dusts, granules, and fine granules; in the range of 40 to 60 weight percent for wettable powders and flowable formulations; and in the range of 30 to 50 weight percent for emulsifiable concentrates, a 3-nitrobenzene sulfonanilide derivative having the formula:

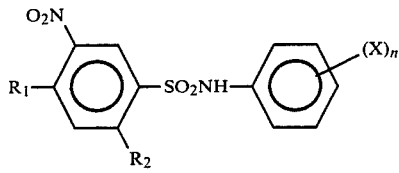

wherein $R_1$ and $R_2$ are both hydrogen, $R_1$ is hydrogen and $R_2$ is methyl or $R_1$ is methyl and $R_2$ is hydrogen, and when $R_1$ and $R_2$ are both hydrogen, $(X)_n$ is 2,4,6-trichloro, 2-chloro-4-nitro or 2-chloro-5-nitro; when $R_1$ is hydrogen and $R_2$ is methyl, $(X)_n$ is 4-iodo, 2,5-dichloro, 3,5-dichloro, 2-bromo-4,5-dichloro or 2-chloro-4-nitro; and when $R_1$ is methyl and $R_2$ is hydrogen, $(X)_n$ is 4-iodo, 2,3-dichloro, 2,5-dichloro, 3,5-dichloro, 2-bromo-4,5-dichloro, 2-chloro-5-nitro, 2-methyl-6-nitro or 2-nitro-4-methyl.

4. The fungicidal composition of claim 3 wherein, in the general formula (I), $(X)_n$ is 2-chloro-4-nitro, $R_1$ is a hydrogen atom and $R_2$ is a methyl radical.

5. The fungicidal composition of claim 3 which is effective in controlling clubroot disease of Brassica spp.

6. The fungicidal composition of claim 4 which is effective in controlling clubroot disease of Brassica spp.

7. A method of controlling clubroot disease of Brassica spp. which comprises, prior to the planting of a crop of the genus Brassica, applying a 3-nitrobenzene sulfonanilide derivative to the field in an amount of 5 to 20 kilograms per hectare, the 3-nitrobenzene sulfonanilide derivative having the general formula:

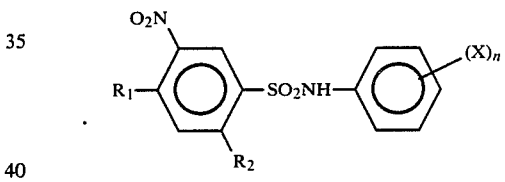

wherein $R_1$ and $R_2$ each represent a hydrogen atom or a methyl radical, X represents a halogen atom, a methyl radical, or a nitro group, n is a whole number of 1 to 3, and when n is equal to 2 or 3, the atoms or radicals represented by X may be identical to or different from each other but the four compounds in which $R_1$ and $R_2$ are both hydrogen atoms and $(X)_n$ is 4-chloro, 3,4-dichloro, 2,4-dichloro or 2,5-dichloro and the compound in which $R_1$ is a methyl radical, $R_2$ is a hydrogen atom and $(X)_n$ is 2-chloro-4-nitro are excluded.

8. The method of claim 7 wherein, in the general formula (I), $(X)_n$ is 2-chloro-4-nitro, $R_1$ is a hydrogen atom and $R_2$ is a methyl radical.

* * * * *